US009868947B2

(12) United States Patent
Gurnett et al.

(10) Patent No.: US 9,868,947 B2

(45) Date of Patent: Jan. 16, 2018

(54) COMPOSITIONS AND METHODS FOR THE CONSTRUCTION OF A RANDOM ALLELIC SERIES

(71) Applicant: Washington University, St. Louis, MO (US)

(72) Inventors: Christine Gurnett, St. Louis, MO (US); Gabriel Haller, St. Louis, MO (US); Matthew Dobbs, St. Louis, MO (US); David Alvarado, St. Louis, MO (US)

(73) Assignees: WASHINGTON UNIVERSITY, St. Louis, MO (US); SHRINERS HOSPITALS FOR CHILDREN, Tampa, FL (US)

( * ) Notice: Subject to any disclaimer, the term of this patent is extended or adjusted under 35 U.S.C. 154(b) by 0 days.

(21) Appl. No.: 15/146,621

(22) Filed: May 4, 2016

(65) Prior Publication Data

US 2016/0326517 A1 Nov. 10, 2016

Related U.S. Application Data

(60) Provisional application No. 62/156,651, filed on May 4, 2015.

(51) Int. Cl.
*C12P 19/40* (2006.01)
*C12N 15/10* (2006.01)

(52) U.S. Cl.
CPC ....... *C12N 15/1031* (2013.01); *C12N 15/102* (2013.01); *C12N 15/1058* (2013.01); *C12N 15/1093* (2013.01); *C12P 19/40* (2013.01)

(58) Field of Classification Search
None
See application file for complete search history.

(56) References Cited

U.S. PATENT DOCUMENTS

| | | | |
|---|---|---|---|
| 5,302,509 | A | 4/1994 | Cheeseman |
| 5,763,594 | A | 6/1998 | Hiatt et al. |
| 5,808,045 | A | 9/1998 | Hiatt et al. |
| 5,872,244 | A | 2/1999 | Hiatt et al. |
| 6,214,987 | B1 | 4/2001 | Hiatt et al. |
| 6,232,465 | B1 | 5/2001 | Hiatt et al. |
| 2003/0215862 | A1 | 11/2003 | Parce et al. |
| 2011/0046359 | A1 | 2/2011 | Lee et al. |
| 2014/0242579 | A1 | 8/2014 | Zhou et al. |

FOREIGN PATENT DOCUMENTS

| | | |
|---|---|---|
| WO | 2004018497 A2 | 3/2004 |
| WO | 2008037568 A2 | 4/2008 |

OTHER PUBLICATIONS

Cirino, P. et al., “Generating Mutant Libraries Using Error-Prone PCR,” Meth. Mol. Biol., 2003, pp. 3-9, Chapter 1, vol. 231, Humana Press Inc., Totowa, NJ.

Copp, J. et al., “Error-Prone PCR and Effective Generation of Gene Variant Libraries for Directed Evolution,” Meth. Mol. Biol., 2014, pp. 3-22, vol. 1179, Springer Science+Business Media, New York.

Findlay, G. et al., “Saturation editing of genomic regions by multiplex homology—directed repair,” Nature, Sep. 4, 2014, pp. 120-123, vol. 513, with Methods, 12 pgs., Macmillan Publishers Limited.

Haller, G. et al., “Functional Characterization Improves Associations between Rare Non-Synonymous Variants in CHRNB4 and Smoking Behavior,” PLoS One, May 2014, pp. 1-15, vol. 9, No. 5, e96753.

Haller, G. et al., “Massively parallel single-nucleotide mutagenesis using reversibly terminated inosine,” Nat. Methods, Nov. 2016, pp. 923-924, vol. 13, No. 11, with Online Methods, 1 pg., Nature America, Inc.

Hutter, D. et al., “Labeled Nucleoside Triphosphates with Reversibly Terminating Aminoalkoxyl Groups,” NIH Publi Access Author Manuscript, available in PMC Dec. 10, 2013, pp. 1-18, Published in final edited form as: Nucleosides Nucleotides Nucleic Acids, Nov. 2010, pp. 879-895, vol. 29, No. 11.

Kitzman, J. et al., “Massively parallel single-amino-acid mutagenesis,” Nat. Methods, Mar. 2015, pp. 203-206, vol. 12, No. 3, with Online Methods, 2 pgs., Nature America, Inc.

Loakes, D., “Survey and Summary. The applications of universal DNA base analogues,” Nucl. Acid Res., 2001, pp. 2437-2447, vol. 29, No. 12, Oxford University Press.

McCullum, E. et al., “Random Mutagenesis by Error-Prone PCR,” Met. Mol. Biol., 2010, pp. 103-109, vol. 634, Springer Science+Business Media, LLC.

Metzker, M. et al., “Termination of DNA synthesis by novel 3'-modified-deoxyribonucleoside 5'-triphosphates,” Nucl. Acid Res., 1994, pp. 4259-4267, vol. 22, No. 20, Oxford University Press.

Patwardhan, R. et al., “High-resolution analysis of DNA regulatory elements by synthetic saturation mutagenesis,” Nat. Biotechnol., Dec. 2009, pp. 1173-1175, vol. 27, No. 12, Nature America, Inc.

Patwardhan, R. et al., “Massively parallel functional dissection of mammalian enhancers in vivo,” Nat. Biotechnol., Mar. 2012, pp. 265-270, vol. 30, No. 3, with Online Methods, 3 pgs., Nature America, Inc.

Smith, R. et al., “Massively parallel decoding of mammalian regulatory sequences supports a flexible organizational model,” Nat. Genet, Sep. 2013, pp. 1021-1028, vol. 45, No. 9, with Online Methods, 2 pgs., Nature America, Inc.

Spee, J. et al., “Efficient random mutagenesis method with adjustable mutation frequency by use of PCR and dITP,” Nucl. Acids Res., 1993, pp. 777-778, vol. 21, No. 3, Oxford University Press.

Starita, L. et al., “Massively Parallel Functional Analysis of BRCA1 Ring Domain Variants,” Genet., Jun. 2015, pp. 413-422, vol. 200, No. 2, with Supporting Information, 13 pgs., Genetics Society of America.

(Continued)

*Primary Examiner* — Christopher M Gross

(74) *Attorney, Agent, or Firm* — Polsinelli PC

(57) ABSTRACT

The present disclosure provides a method of making a systematic single point mutation in a target nucleic acid and a method of generating a mutational library comprising target nucleic acids with single point mutations. The mutational library comprises target nucleic acids with single point mutations distributed evenly throughout the target nucleic acid.

20 Claims, 9 Drawing Sheets
(7 of 9 Drawing Sheet(s) Filed in Color)

(56) References Cited

OTHER PUBLICATIONS

Stiffler, M. et al., "Evolvability as a Function of Purifying Selection in TEM-1 beta-Lactamase," Cell, Feb. 26, 2015, pp. 882-892, vol. 160, No. 5, Elsevier Inc.

COMPOSITIONS AND METHODS FOR THE CONSTRUCTION OF A RANDOM ALLELIC SERIES

CROSS REFERENCE TO RELATED APPLICATIONS

This application claims the benefit of U.S. Provisional Application No. 62/156,651, filed May 4, 2015, the disclosure of which is hereby incorporated by reference in its entirety.

GOVERNMENTAL RIGHTS

This invention was made with government support under R01AR067715-01 awarded by the NIH. The government has certain rights in the invention.

FIELD OF THE INVENTION

The present disclosure provides a method of making a systematic single point mutation in a target nucleic acid and a method of generating a mutational library comprising target nucleic acids with single point mutations. The mutational library comprises target nucleic acids with single point mutations distributed evenly throughout the target nucleic acid.

BACKGROUND OF THE INVENTION

Accurate, inexpensive and efficient methods of large scale mutagenesis of specific DNA sequences have the potential to allow for rapid assessment of the effects of single nucleotide changes on protein function. These methods remain limited by the need to synthesize oligonucleotides en masse to be used as templates for mutagenesis. Currently, the construction of allelic series requires the purchase of many hundreds to thousands of oligonucleotides of 10s of bases to hundreds of bases with specific sequences. Thus, there is a need in the art for a new method of single nucleotide mutagenesis where the purchase of these oligos is no longer required to produce allelic series pools.

Such a novel method would allow for the construction of pools of DNA sequences that differ from the normal form by one and only one base allowing for the rapid production of allelic series to be used in structure-function studies. This method would aid in the interpretation of variants observed in human patients of unknown significance and for in vitro protein evolution and engineering.

SUMMARY OF THE INVENTION

In an aspect, the disclosure provides a method of generating a mutational library of a target nucleic acid. The method comprises: (a) creating a reaction mixture comprising the target nucleic acid, polymerase, a forward primer, deoxynucleotide triphosphates (dNTPs) and universal base triphosphates comprising a blocking group; (b) performing linear PCR, wherein the linear PCR generates products of various lengths, wherein each product comprises about 1 universal base comprising a blocking group, and wherein the linear PCR stops after incorporating the universal base triphosphate comprising a blocking group; (c) removing the blocking group from the universal base incorporated into the linear product; (d) extending the products from (c) with polymerase, wherein the extension products comprise about 1 universal base incorporated therein; and (e) performing exponential PCR, wherein the products from (d) are amplified and wherein the products comprise a single point mutation in the location where the universal base was incorporated. The products of the exponential PCR make up a mutational library of the target nucleic acid comprising a plurality of products each comprising a single point mutation. The point mutations are evenly distributed throughout the products of the mutational library.

In another aspect, the disclosure provides a method of making 2'-deoxy, 3'-O—NH2 inosine triphosphate from 2'-deoxy, 3'-O—NH2 adenosine triphosphate. The method comprises: (a) dephosphorylating 2'-deoxy, 3'-O—NH2 adenosine triphosphate with a phosphatase; (b) deaminating the product from (a) with a deaminase; and (c) phosphorylating the product from (b) with three different kinases.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) Schematic of SAS mutagenesis: 1) Linear amplification of a target genomic region is performed using a mixture of dNTPs and reversibly-terminated dITP and a biotinylated primer; 2) The termination of products from step 1 is reversed and products are extended using the original template; and 3) Reverse primer is added for one cycle, products are hybridized with streptavidin coated magnetic beads and washed to remove template. PCR is then performed to introduce single point mutations across from each inosine on the forward strand. (FIG. 1B) Distribution of mutations per molecule in a representative SAS library. Bars represent the proportion of reads harboring the stated number of mutations. The majority of SAS mutant clones harbor one mutation while earlier dIPT doping method (adding a proportion of dITP directly to a PCR) increases mutation rate but retains Poisson distributed mutational load. Greater than 99% of reads harbored zero mutations when PCR amplified using dNTPs only with Pfu ultra polymerase. (FIG. 1C) Distribution of single base mutations in β-Lactamase SAS library. Points are color coded by the nucleotide to which the base was changed. Counts are singly mutated molecules per 1 million reads.

(FIG. 2A) Functional map of mutation effect sizes for all possible single nucleotide changes. Y-axis indicates nucleotide 141 of the TEM-1 β-lactamase gene (top, AA 47) to nucleotide 315 (bottom, AA 105). Non-conservative amino acid changes are those that alter the amino acid character, i.e. hydrophobic to nonpolar. Conservative changes are non-synonymous changes that do not alter the amino acid type. Sites S70 and K73 within the active site are labeled. (FIG. 2B) Crystal structure of TEM-1 β-lactamase with mutated sites pictured with space filled molecular model and non-tested sites with backbone only. Sites are colored according to their log 2 effect size after ampicillin selection with red indicating a greater effect size.

DETAILED DESCRIPTION OF THE INVENTION

Figure 1A:
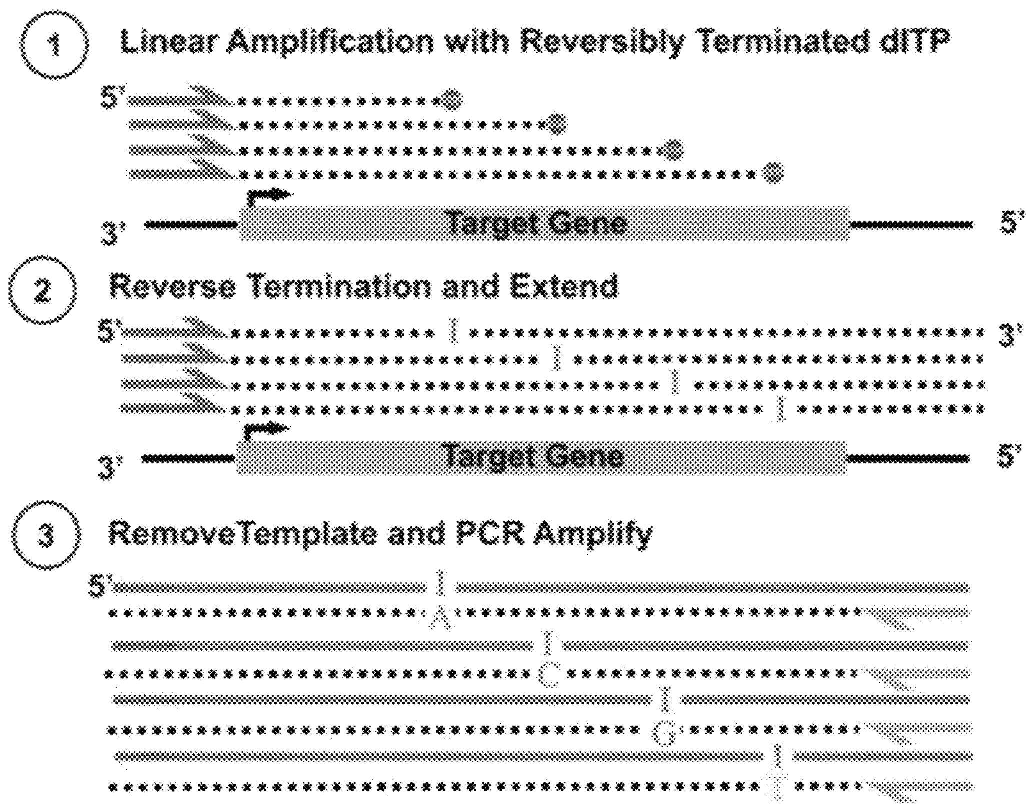
FIG. 1A, FIG. 1B and FIG. 1C depict schematic and library characteristics of SAS mutagenesis.

The present invention provides methods of making a random single point mutation in a target nucleic acid as well as generating a mutational library comprising products each with a single point mutation. Importantly, the library of products has the single point mutation distributed evenly throughout the molecule.

I. Method of Generating a Systematic Allelic Series

Generally speaking, the method comprises creating a reaction mixture comprising the target nucleic acid, polymerase, a forward primer, deoxynucleotide triphosphates (dNTPs) and universal base triphosphates comprising a blocking group; performing linear PCR, wherein the linear PCR generates a product comprising about 1 universal base comprising a blocking group and wherein the linear PCR stops after incorporating the universal base triphosphate comprising a blocking group; removing the blocking group from the universal base incorporated into the linear product; extending the product with polymerase, wherein the extension product comprises about 1 universal base incorporated therein; and performing exponential PCR, wherein the extension product is amplified and wherein the product comprises a single point mutation in the location where the universal base was incorporated. This method may be used to generate a mutational library of a target nucleic acid with single point mutations, wherein the mutational library comprises target nucleic acids with single point mutations evenly distributed throughout the target nucleic acid.

Thus, the invention improves upon the prior art in at least the following ways: (i) allows for the incorporation of a single nucleotide change in a target nucleic acid sequence (i.e. one and only one mutation per target nucleic acid sequence); (ii) each single nucleotide change is distributed evenly throughout the target nucleic acid sequence of the mutational library; and (iii) a mutational library is generated comprising each possible nucleotide at the mutant position. This is a significant improvement upon methods in the prior art of generating a mutational library either via oligonucleotide methods or other universal base methods. The methods disclosed herein are quick and cost-effective.

(a) Linear PCR

A method of the invention involves creating a reaction mixture comprising a target nucleic acid, polymerase, a forward primer, deoxynucleotide triphosphates (dNTPs) and universal base triphosphates comprising a blocking group and performing linear PCR. The linear PCR generates a product comprising about 1 universal base comprising a blocking group. Importantly, the linear PCR stops after incorporating the universal base comprising a blocking group. The reaction mixture may also comprise salts and buffers essential for optimal activity of the polymerase in the reaction. Universal base triphosphates comprising a blocking group are as described in Section II.

A target nucleic acid may be any nucleic acid amenable to standard PCR. A target nucleic acid may be from any sample that contains nucleic acid molecules. The target nucleic acid may be from humans, animals, plants, microorganisms or viruses. In certain embodiments, the target nucleic acid is from a human. The target nucleic acid may be DNA, RNA, or a complementary DNA (cDNA) sequence that is synthesized from a mature messenger RNA. If the nucleic acid template is RNA, the RNA may be reverse transcribed to DNA using methods well known to persons skilled in the art. In a preferred embodiment, the target nucleic acid is DNA. In some embodiments, suitable quantities of target nucleic acid for the invention may be 10, 9, 8, 7, 6, 5, 4, 3, 2, 1, 0.5, 0.1, 0.05, 0.01, 0.005, 0.001 μg or less. In other embodiments, suitable quantities of target nucleic acid for the invention may be 1000, 900, 800, 700, 600, 500, 400, 300, 200, 100, 75, 50, 25, 10, 1, 0.5, 0.1 ng or less.

A polymerase may be any polymerase that is capable of incorporating the universal base comprising a blocking group. In certain embodiments, the polymerase is a thermostable polymerase. Non-limiting examples of thermostable polymerases may include polymerases isolated from the thermophilic bacteria *Thermus aquaticus* (Taq polymerase), *Thermus thermophilus* (Tth polymerase), *Thermococcus litoralis* (Tli or VENT™ polymerase), *Pyrococcus furiosus* (Pfu or DEEPVENT™ polymerase), *Pyrococcus* woosii (Pwo polymerase) and other *Pyrococcus* species, *Bacillus stearothermophilus* (Bst polymerase), *Sulfolobus acidocaldarius* (Sac polymerase), Thermoplasma *acidophilum* (Tac polymerase), *Thermus* rubber (Tru polymerase), *Thermus* brockianus (DYNAZYME™ polymerase) *Thermotoga neapolitana* (Tne polymerase), *Thermotoga* maritime (Tma) and other species of the *Thermotoga* genus (Tsp polymerase), and *Methanobacterium thermoautotrophicum* (Mth polymerase). Variants of thermostable polymerases that accept universal base triphosphates comprising a blocking group are known in the art. More specifically, variants of thermostable polymerases that accept universal base triphosphates that have a 3'-O—$NH_2$ group are known in the art. For example, see Chen et al., *Proc Natl Acad Sci USA* 2010; 107: 1948-1953. In a specific embodiment, the polymerase is POL475 (Firebird 475) from FireBird Bio, LLC.

A forward primer comprises a target specific sequence. The target specific sequence is a sequence complementary to a target nucleic acid. The target specific sequence may be altered based on the target nucleic acid to be amplified. Generally, a primer may be synthesized using the four naturally occurring deoxynucleotides dATP, dTTP, dCTP and dGTP. A primer may be designed using standard primer design computer software techniques known to individuals skilled in the art. The variables considered during primer design may include primer length, GC pair content, melting temperature, and size of the target nucleic acid. Generally speaking, primers should not form hairpin structures or self- or hetero-primer pairs. In an embodiment, a primer may comprise a sequence of 15, 20, 25, 30, 35, 40, 45, 50 or more bases complementary to a portion of a target nucleic acid. In another embodiment, a primer melting temperature may be 50, 55, 60, 65, 70 or 75° C. In certain embodiments, the forward primer may further comprise an affinity label for purification. An affinity label has affinity for a cognate binding partner which may be used for affinity purification. For example, a forward primer may further comprise a biotin, digoxigenin and/or dinitrophenol. In a specific embodiment, a forward primer is biotinylated. The purification moiety may be used to isolate the linear PCR product. For example, when the forward primer is biotinylated, the linear PCR product may be isolated using avidin or streptavidin beads. Methods of affinity purification using biotin-streptavidin are known in the art. Such a method may be used to isolate the linear PCR product from the reaction mixture. Optionally, prior to isolation of the linear PCR product from the reaction mixture, the contents of the linear PCR reaction may be run on an agarose gel and products >20 base pairs and <full length may be excised and then subjected to affinity purification. This added step removes full length product that would not have incorporated a universal base comprising a blocking group as well as unextended primers.

The deoxynucleotide triphosphates added the reaction include the four naturally occurring deoxynucleotides dATP, dTTP, dCTP and dGTP.

For the linear PCR reaction, forward primer is contacted with target nucleic acid. In an embodiment, a linear PCR reaction may comprise target nucleic acid, forward primer, polymerase, water, buffer, deoxynucleotide triphosphates (dNTPs), and universal base triphosphates comprising a blocking group in a single reaction vial. The pool of triphosphates may comprise about 50% dNTPs and about 50% universal base triphosphates comprising a blocking group. Alternatively, the pool of triphosphates may comprise about 40%, about 45%, about 50%, about 55%, about 60% dNTPs and about 60%, about 55%, about 50%, about 45%, about 40% universal base triphosphates comprising a blocking group, respectively. Stated another way, the deoxynucleotide triphosphates (dNTPs) and universal base triphosphates may added to the reaction mixture in about a 1:1 ratio. Linear PCR may be performed according to standard methods in the art. By way of non-limiting example, the linear PCR reaction may comprise denaturation, followed by about 25 cycles of denaturation, annealing and extension.

According to a method of the invention, performing linear PCR generates products comprising about 1 universal base comprising a blocking group. Although 1 universal base is preferred, it is possible that 2 universal bases may be incorporated. However, these products are not as useful as those comprising 1 universal base. Thus, in a preferred embodiment, 1 universal base is incorporated. Importantly, the linear PCR stops after incorporating the universal base comprising a blocking group. Because where the universal base comprising a blocking group is incorporated is random, products of various lengths are generated. See FIG. 1A, step 1. Advantageously, using a method of the invention there is not a bias for the beginning of the target nucleic acid. In previous methods of generating a mutagenesis library, the majority of mutated target nucleic acids comprise more than one mutation. Further, when a target nucleic acid with a single mutation is generated, there is a strong bias of this mutation being toward the 5' end of the target nucleic acid. Advantageously, the method disclosed herein provides for a mutagenesis library comprising target nucleic acids with a single mutant. Additionally, it was unexpectedly discovered that there is no bias for the 5' end of the target nucleic acid. Instead, it was surprisingly found that the mutagenesis library comprises nucleic acids with single point mutations distributed evenly throughout the products in the mutagenesis library. As such, when generating a mutational library comprising single point mutants of a target nucleic acid, the library will contain products with the single point mutant distributed evenly throughout the length of the target nucleic acid sequence.

(b) Reverse Termination and Extension

A method of the invention further comprises removing the blocking group from the universal base incorporated into the linear PCR product. The removal of the blocking group allows polymerase to extend from the incorporated universal base. The extension product comprises about 1 universal base incorporated therein. See FIG. 1A, step 2. Thus, the process of reverse termination and extension results in a product comprising the sequence of the target nucleic acid but with a single universal base incorporated therein.

As described above, during linear PCR, the universal base triphosphate comprising a blocking group was incorporated into the growing polynucleotide thereby terminating extension. The next step in the process is reverse termination. Reverse termination may be accomplished by cleavage of the universal base to remove the blocking group. The cleaving step may be accomplished by various means including, but not limited to, chemical means, photo-cleavage, and enzymatic removal. In a specific embodiment, the blocking group is removed by exposure to 70 mM sodium nitrite buffer, pH 5.5. Removal of the blocking group reactivates or releases the growing polynucleotide strand, freeing it to be available for subsequent extension by the polymerase enzyme. Extension of the linear PCR product via polymerase may be accomplished by methods standard in the art. Extension of the linear PCR product may be carried out for about 1 to about 10 cycles. For example, extension of the linear PCR product may be carried out for 1, 2, 3, 4, 5, 6, 7, 8, 9, or 10 cycles. In a specific embodiment, extension of the linear PCR product is carried out for 8 cycles. In an embodiment, the polymerase is a high-fidelity polymerase. Non-limiting examples of high-fidelity polymerases include Q5® High-Fidelity DNA Polymerase, Phusion® High-Fidelity DNA Polymerase, Platinum® Taq DNA Polymerase High Fidelity, Accura® High-Fidelity Polymerase, iProof™ High-Fidelity DNA Polymerase, Integrity High Fidelity Polymerase, Platinum SuperFi DNA Polymerase, AccuPrime™ Taq DNA Polymerase High Fidelity, Platinum® Pfx DNA Polymerase, and Pfu or PfuTurbo® DNA polymerase. In a specific embodiment, the high-fidelity polymerase is Q5® High-Fidelity DNA Polymerase.

In certain embodiments, the linear PCR products are isolated prior to removal of the blocking group. For example, if the forward primer comprises an affinity label for purification, then the linear PCR products may be purified using the affinity label's cognate binding partner. Alternatively, the linear PCR products may be column purified. When using column purification, it may be necessary to develop a linear primer such that the shortest products (i.e. when the universal base is incorporated at positions 1-70) are not lost during column purification. This may be done be designing a forward primer that is upstream of the start codon for the target nucleic acid. In other embodiments, the linear PCR products are isolated after removal of the blocking group. This may be as described above. In certain embodiments, the linear PCR products are isolated prior to removal of the blocking group and after removal of the blocking group. In specific embodiments, a forward primer comprising an affinity label facilitates the isolation.

(c) Exponential PCR

A method of the invention further comprises contacting the extension product with a forward and reverse primer. The forward primer may be the same or different from the forward primer described in Section 1(a). A reverse primer comprises a target specific sequence downstream of the forward primer. Generally, a primer may be synthesized using the four naturally occurring deoxynucleotides dATP, dTTP, dCTP and dGTP. A primer may be designed using standard primer design computer software techniques known to individuals skilled in the art. The variables considered during primer design may include primer length, GC pair content, melting temperature, and size of the target nucleic acid. Generally speaking, primers should not form hairpin structures or self- or hetero-primer pairs. In an embodiment, a primer may comprise a sequence of 15, 20, 25, 30, 35, 40, 45, 50 or more bases complementary to a portion of a target nucleic acid. In another embodiment, a primer melting temperature may be 50, 55, 60, 65, 70 or 75° C. In one embodiment, the melting temperature of each primer of the primer pair may be the same. In another embodiment, the melting temperature of each primer of the primer pair may be different for each primer. In yet another embodiment, the difference in melting temperatures between each primer of the primer pair may be 1, 2, 3, 4, 5, 6, 7, 8, 9° C. or more. In another embodiment, the maximum difference in melting temperature between primer pairs may be 5° C. In an embodiment, the GC content of primer may be 10, 20, 30, 40, 50, 60, 70 or 80%. In yet another embodiment the primer pair may be designed to amplify nucleic acid target products that may be about 30, about 40, about 50, about 60, about 70, about 80, about 90, about 100, about 200, about 300, about 400, about 500, about 600, about 700, about 800, about 900, about 1000, about 1500, about 2000, about 2500, about 3000, about 4500, about 5000, about 5500, about 6000, about 6500, about 7000, about 7500, about 8000, about 8500, about 9000, about 9500, about 10,000 or more base pairs in length.

In an embodiment where the target nucleic acid to be amplified is long, a forward primer or a reverse primer may further comprise a unique molecular identifiable (UMI) sequence, also referred to as a barcode, and an adapter. See, for example, FIG. 6. A long target nucleic acid to be amplified may be greater than 500, greater than 600, greater than 700, greater than 800, greater than 900, greater than 1000, greater than 1500, greater than 2000, greater than 2500, greater than 3000, greater than 4500, greater than 5000, greater than 5500, greater than 6000, greater than 6500, greater than 7000, greater than 7500, greater than 8000, greater than 8500, greater than 9000, greater than 9500, or greater than 10,000 base pairs in length. As used herein, a "unique molecular identifiable (UMI) sequence" or "barcode" is composed of random nucleotides to generate a complexity of UMI sequences far greater than the number of unique products to be sequenced. In an embodiment, the UMI sequences may be about 5 to about 100 nucleotides. In another embodiment, the UMI sequences may be about 10 to about 25 nucleotides. For example, the UMI sequences may be about 15 to about 20 nucleotides. In still another embodiment, the UMI sequences are about 20 nucleotides. Accordingly, the UMI sequences may be 10, 11, 12, 13, 14, 15, 16, 17, 18, 19, 20, 21, 22, 23, 24 or 25 or more nucleotides. In a specific embodiment, a reverse primer further comprises a UMI sequence and an adapter. As used herein, an "adapter" is a sequence that permits universal amplification. A key feature of the adapter is to enable the unique amplification of the product only without the need to remove existing template nucleic acid or purify the products. This feature enables an "add only" reaction with fewer steps and ease of automation. The adapter may be Y-shaped, U-shaped, hairpin-shaped, or a combination thereof. In a specific embodiment, the adaptor is Y-shaped. In another embodiment, the adapter may be an Illumina adapter for Illumina sequencing.

For the exponential PCR reaction, a reaction mixture comprises the extension product, polymerase, a forward primer, a reverse primer, and deoxynucleotide triphosphates (dNTPs). The reaction mixture may also comprise salts and buffers essential for optimal activity of the polymerase in the reaction. Exponential PCR may be performed according to standard methods in the art. By way of non-limiting example, the exponential PCR reaction may comprise denaturation, followed by about 25 cycles of denaturation, annealing and extension, followed by a final extension. In an exemplary embodiment, the exponential PCR reaction comprises denaturation at 98° C. for 30 seconds, followed by 25 cycles of (98° C. for 10 seconds, 50° C. for 30 seconds, 72° C. for 30 seconds), followed by a final extension at 72° C. for 2 minutes.

Upon performing exponential PCR, the extension PCR products are amplified. Importantly, during amplification, when a universal base is encountered any of the dNTPs provided in the reaction mixture may be incorporated in its place. Thus, a product is generated comprising the sequence of the target nucleic acid but with a single nucleotide change. See FIG. 1A, step 3. By performing exponential PCR, it is possible to generate a product comprising the sequence of the target nucleic acid with each nucleotide at a single position. Thus, the invention allows for (i) the incorporation of a single nucleotide change in a target nucleic acid sequence; (ii) each single nucleotide change is distributed evenly throughout the target nucleic acid sequence of the mutational library; and (iii) a mutational library is generated comprising each possible nucleotide at the mutant position. This is a significant improvement upon methods in the prior art of generating a mutational library either via oligonucleotide methods or other universal base methods.

In certain embodiments, the extension product is isolated from the sample prior to exponential PCR via degradation of remaining linear primer and target nucleic acid. For example, exonucleases may be added to the reaction mixture at the completion of the extension to degrade remaining linear primer and target nucleic acid. In other embodiments, uracil-DNA-glycosylase may be added to the reaction. In still other embodiments, an enzyme that cleaves methylated DNA may be added to the reaction. In certain embodiments, DpnI may be added to the reaction. Alternatively, the forward or reverse primer used for exponential PCR may comprise an affinity label for purification such that the exponential PCR products may be purified using the affinity label's cognate binding partner.

In an embodiment, more than 30% of the exponential PCR products comprise a single nucleotide change relative to the target nucleic acid. For example, more than 30%, more than 35%, more than 45%, more than 50%, more than 55%, more than 60%, more than 65%, more than 70%, more than 75%, more than 80%, more than 85%, more than 90%, or more than 95% of the exponential PCR products comprise a single nucleotide change relative to the target nucleic acid. Importantly, less than 5% of the exponential PCR products comprise more than a single nucleotide change relative to the target nucleic acid. For example, less than 4%, less than 3%, less than 2%, or less than 1% of the exponential PCR products comprise more than a single nucleotide change relative to the target nucleic acid.

The exponential PCR products may then be sequenced. Sequencing may be performed according to standard methods in the art. When long target nucleic acids are sequenced, overlapping products may be generated. For example, the reverse primer comprising the UMI sequence and adapter may be kept the same and different forward primers may be used which are complementary to the target nucleic acid at varying distances from the reverse primer. Sequencing may then be performed on a massively parallel sequencing platform, many of which are commercially available including, but not limited to Illumina, Roche/454, Ion Torrent, and PacBIO. In a specific embodiment, Illumina sequencing is used. Sequencing reads obtained may then be collapsed based on their UMI and variants may be called using the consensus sequence for all UMI sequences with >20 reads.

II. Universal Base Triphosphate Comprising a Blocking Group

A method of the invention requires the use of a universal base triphosphate comprising a blocking group. As used herein, a "universal base" forms base pairs with each of the natural DNA/RNA bases with little discrimination between them. Non-limiting examples of universal bases include ribo-hypoxanthine, 2'-deoxyribonucleoside, 3-nitropyrrole, 5-nitroindole, 4-nitroindole, 6-nitroindole, 2'-dexoyinosine and analogs thereof such as 2'-deoxyisoinosine, 7-deaza-2'-deoxyinosine, 2-aza-2'-deoxyinosine, 4-nitrobenzimidazole, acyclic sugar analogues of hypoxanthine, 5-nitroindazole, 4-aminobenzimidazole, phenyl C-ribonucleoside and its 2'-deoxyribosyl nucleoside, imidazole 4,5-dicarboxamide, 3-nitroimidazole. For a review of universal bases that may be used herein see Loakes, Nucl Acids Res 2001; 29(12): 2437-2447, which is hereby incorporated by reference in its entirety. In certain embodiments, the universal base may be selected from the group consisting of 3-nitropyrrole, 5-nitroindole, and 2'-dexoyinosine. In a specific embodiment, the universal base is 2'-dexoyinosine.

Once incorporated, the universal base triphosphate comprising a blocking group acts as chain terminator precluding further processing by the polymerase enzyme because the blocking groups prevents further polymerase activity. In other words, the polymerase enzyme cannot utilize the modified nucleotide efficiently as a substrate to continue synthesis.

According to the invention, the blocking group is reversible, meaning the blocking group may be removed by chemical, enzymatic, and/or photo-cleavage processes. In other words, the blocking group is covalently bound to the nucleotide/nucleoside analog but is capable of being hydrolyzed or otherwise removed by any known means. For instance, most commonly such blocking groups may be hydrolyzed chemically or photochemically, or the blocking group may be more specifically removed enzymatically.

Any universal base comprising a suitable blocking group may be used. In certain embodiments, blocking groups may be located at the 2' or 3' position of the sugar moiety. Numerous blocking groups are known in the art. See, for example, Metzker et al., "Termination of DNA synthesis by novel 3'-modified deoxyribonucleoside triphosphates," Nucleic Acids Res., 22:4259-4267, 1994; and U.S. Pat. Nos. 5,872,244; 6,232,465; 6,214,987; 5,808,045; 5,763,594, and 5,302,509; and U.S. Patent Application Publication No. 20030215862; 20110046359; 20140242579; and WO Publication No. 2004018497; 2008037568. In a specific embodiment, the blocking group is 3'-O—$NH_2$.

In certain embodiments, the blocking group is attached to the 3' hydroxyl (3'-OH) of the sugar moiety. Upon binding of a nucleotide triphosphate to a polymerase and addition to the growing polynucleotide chain, which grows in the 5' to 3' direction, the triphosphate moiety on the 5' end of the nucleotide is cleaved by the polymerase enzyme, thereby releasing sufficient energy to covalently link it to the free 3' hydroxyl group of the growing polynucleotide chain. If the 3' hydroxyl of the nucleotide molecule does not contain a blocking group, the polymerase enzyme would simply carry on, adding the next available nucleotide to the growing chain. By incorporating a blocking group, the polynucleotide is not capable of continuing further and the reaction pauses.

The disclosure also provides a method of making 2'-deoxy, 3'-O—$NH_2$ inosine triphosphate from 2'-deoxy, 3'-O—$NH_2$ adenosine triphosphate. For example, see FIG. 3. The method comprises dephosphorylating 2'-deoxy, 3'-O—$NH_2$ adenosine triphosphate with a phosphatase; deaminating the product with a deaminase; and phosphorylating the product with three different kinases. In a specific embodiment, the phosphatase is shrimp alkaline phosphatase. In another specific embodiment, the deaminase is adenosine deaminase. In an embodiment, the deaminating is performed in 50 mM postassium phosphate buffer. In still another specific embodiment, the three different kinases are adenylate kinase, T4 polynucleotide kinase and pyruvate kinase. In certain embodiments, the enzymes are inactivated following the reaction. Enzymes may be inactivated via standard methods, such as, but not limited to heat inactivation or the addition of an inhibitor or chemical. The product may or may not be purified in between steps. The final product may or may not be purified prior to use.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Massively Parallel Single Nucleotide Mutagenesis Using Reversibly-Terminated Inosine Interpretation of genetic variants observed in the human population is a major obstacle confronting precision medicine. Variants are often observed only in a single individual, so that determining the functional effect of specific mutations becomes a crucial step in the assessment of pathogenicity. This process is often labor intensive, slow and cost-prohibitive. We previously demonstrated the utility of functional testing of observed variants by weighting variants by their effect on protein function in vitro. The production and functional assessment of all possible variants in a gene may facilitate predictions of a variant's deleteriousness and for the grouping of variants of similar effect in tests of association, substantially increasing statistical power.

The power and utility of rapid, accurate mutation library production has been recently demonstrated. Several large-scale mutagenesis methods have been utilized to screen both genes and non-coding loci for genetic variants that alter protein function or transcript levels of nearby genes. Mutagenesis libraries have been created using a variety of methods, including the use of error-prone or inosine containing PCR, or use of a large number of long oligonucleotides to synthetically create DNA sequence. However, each of these approaches has their limitations. While error-prone PCR is inexpensive, products often have multiple mutations that confound interpretation of results. The production of long oligonucleotides for direct cloning or short oligonucleotides to use as mutagenic primers requires substantial up-front financial investment for each genetic region being investigated.

Here we demonstrate the construction of a systematic allelic series (SAS) by performing mutagenesis of segments of DNA using reversibly-terminated deoxyinosine triphosphates (rtITPs). By combining cycle termination used in Sanger sequencing, reversible termination used in Illumina sequencing, and the ability of inosine to base pair with each of the four bases, we have systematically incorporated single inosine molecules into DNA molecules allowing the introduction of one and only one mutation per molecule during PCR amplification.

Figure 3:
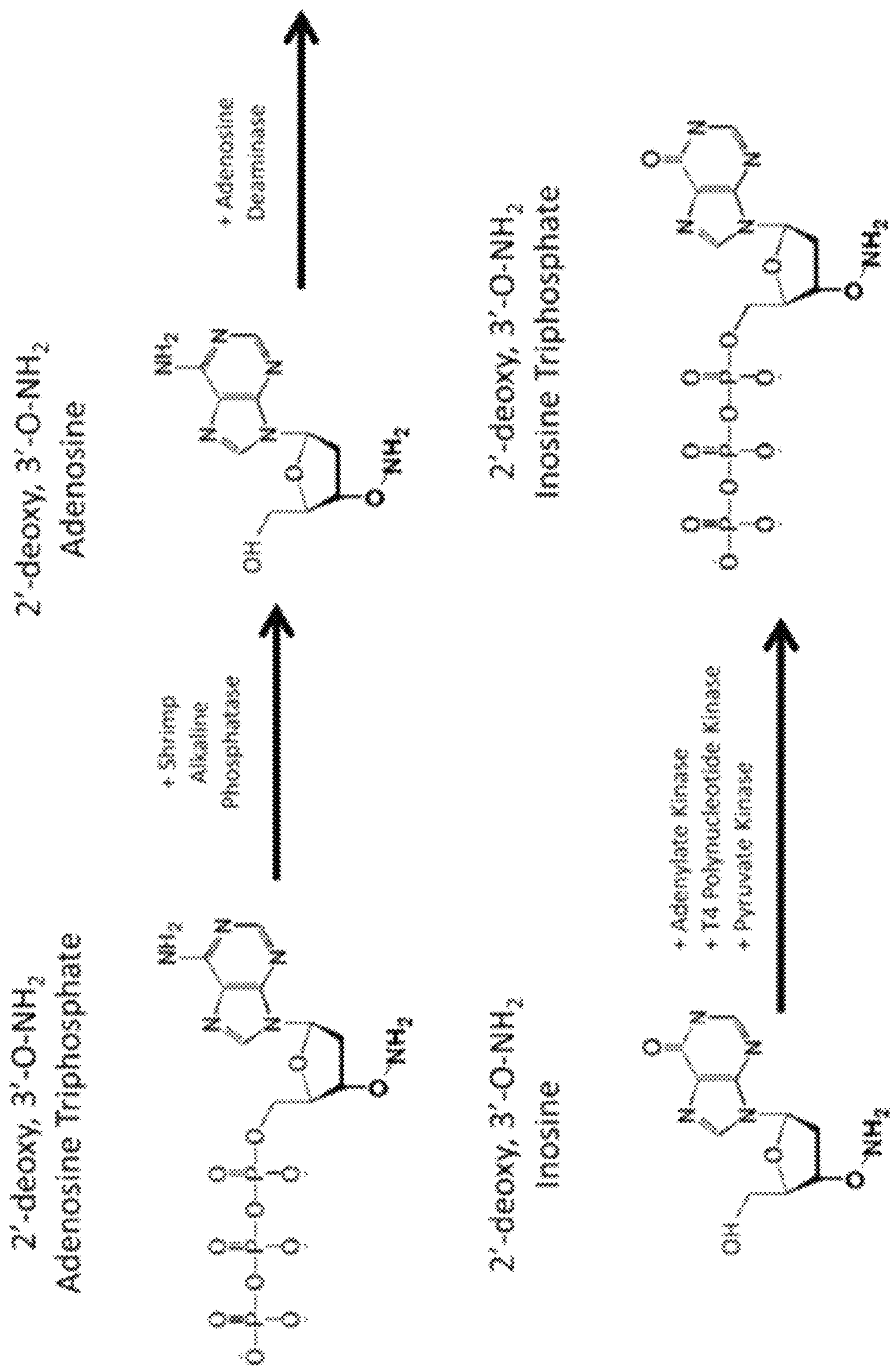
FIG. 3 depicts a schematic of enzymatic creation of reversibly terminated 2'-deoxy, 3'-O—NH2 inosine triphosphate. Due to the inability of adenosine deaminase to convert adenosine triphosphate into inosine triphosphate, we dephosphorylated reversibly-terminated deoxyadenosine triphosphate before deamination. We subsequently re-phosphorylated the newly formed reversibly-terminated deoxyinosine using a mixture of three nucleotide/nucleoside kinases to form a deoxyinosine triphosphate capable of being incorporated into a PCR product.

Briefly, we generated reversibly-terminated deoxyinosine triphosphates (rtITP) by sequential enzymatic reaction of reversibly-terminated deoxyadenosine triphosphates with alkaline phosphatase to remove phosphates, adenosine deaminase to create inosine from adenosine and finally, adenylate kinase, T4 polynucleotide kinase and pyruvate kinase to rephosphorylate (FIG. 3). This multistep process was required due to the inability of adenosine deaminase to deaminate adenosine triphosphate and the lack of commercially available rtITP.

A linear amplification of the sequence of interest was then performed using a biotinylated forward primer, a special polymerase (Firebird 475, Firebird Biomolecular Sciences, LLC) that is required for the efficient incorporation of reversibly-terminated nucleotides, and a dNTP pool containing 50% w/v rtITP generated above (FIG. 1A). Incorporation of rtITP molecules and their termination of polymerase extension was confirmed by amplification with a 5'-ROX-labeled primer with termination occurring at each and every nucleotide position only in the presence of rtITP (FIG. 4), while full-length product was primarily created in the absence of rtITP as expected. For short products, a band consisting of products >20 bp and <full length was extracted from an agarose gel to remove both unwanted full length product that would not have incorporated deoxyinosine triphosphates as well as unextended primers. The systematic series of biotinylated DNA of varying lengths was subsequently isolated by hybridization to streptavidin coated magnetic beads. The 3'-O—NH2 termination moiety on the rtITPs was then removed by exposure of DNA bound beads to sodium nitrite (0.7M, pH 5.5) and the products were extended to full-length using a high-fidelity polymerase. Beads were then washed to remove template DNA and amplified to produce PCR products containing each of the 4 alternative nucleotides at each site where inosines had been incorporated.

Figure 1B:
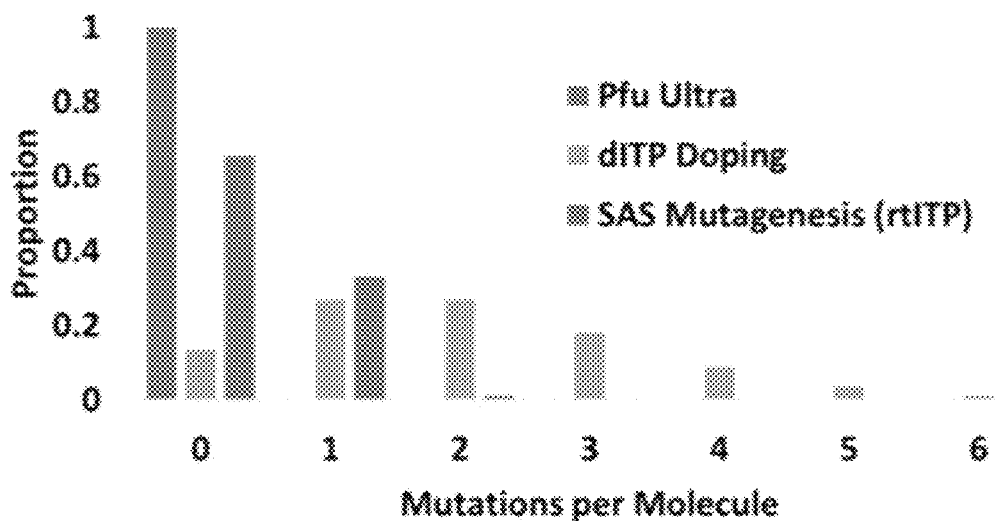
Figure 1C:
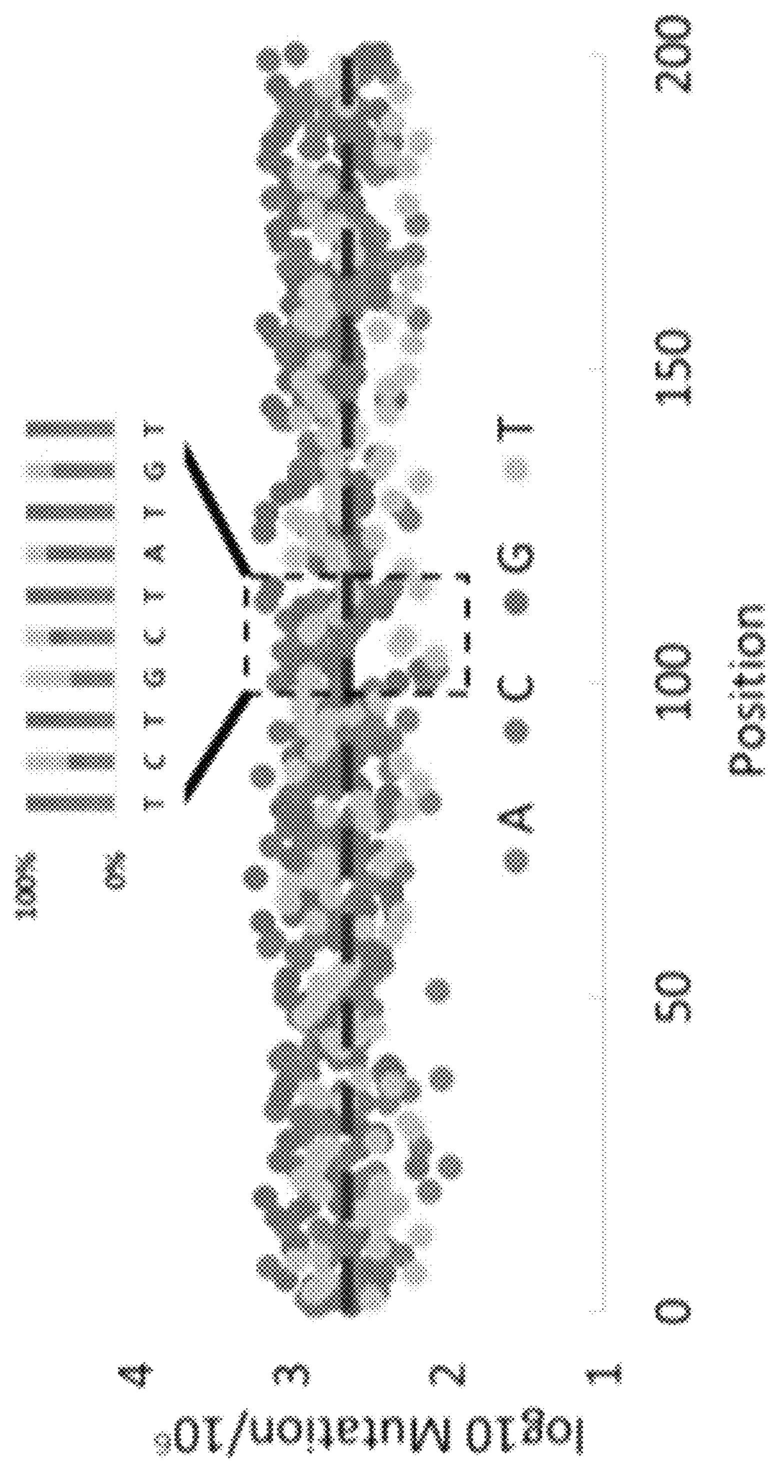

We utilized SAS mutagenesis to create a library of the full-length 861 bp ampicillin resistance gene (AmpR) encoding TEM-1 β-lactamase. As a proof of principle, 217 bp consisting of a portion of the active site of the ampicillin resistance gene was amplified and cloned in-frame into a wild-type β-lactamase plasmid also containing the kanamycin resistance gene, allowing the plasmid library to replicate efficiently without ampicillin selection. Completely overlapping paired-end sequencing of this SAS library unselected for ampicillin resistance revealed that 33% of clones contained one and only one mutation. Importantly, only ~1% of clones contained >1 mutation and 65% contained no mutations (FIG. 1B). This is a marked reduction in secondary mutations compared to previous methods, the most effective of which produced similar rate of single mutations (33-47%) but produced a substantial proportion of molecules with secondary mutations (21-35%). Because the error rate for Illumina MiSeq reads is >10% per read, it was essential to distinguish SAS generated mutations from sequencing errors. For this reason, we initially limited our mutagenesis reactions to <250 bp so that they could be fully sequenced from both directions to distinguish true mutations from sequencing errors. SAS generated mutations were evenly distributed across the region as shown by comprehensive coverage of single nucleotide changes supported by >300 reads for each possible single base with similar substitution rates of each of four possible nucleotides (FIG. 1C).

Figure 2A:
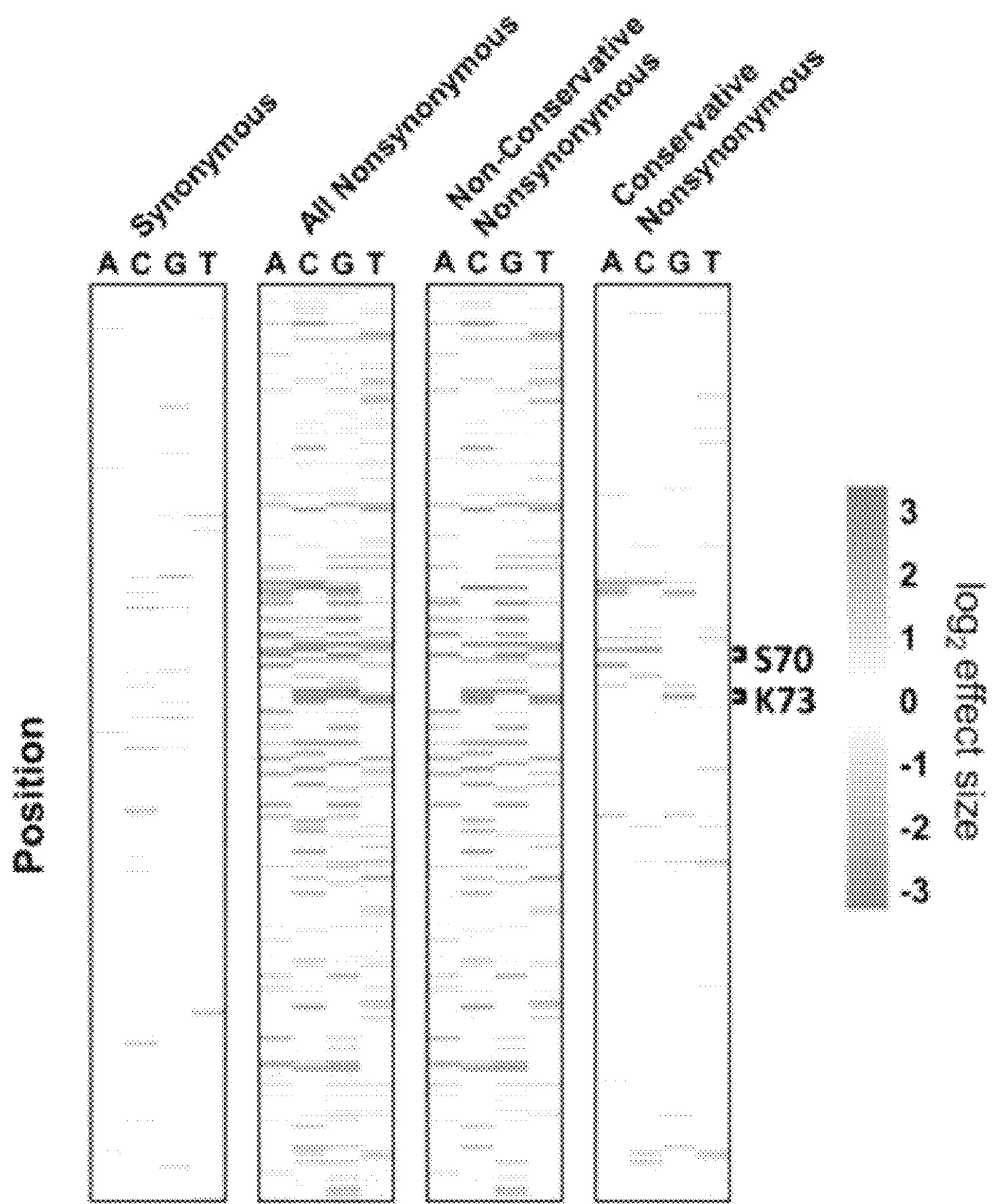
FIG. 2A and FIG. 2B depict functional selection of β-lactamase SAS mutational library.
Figure 2B:
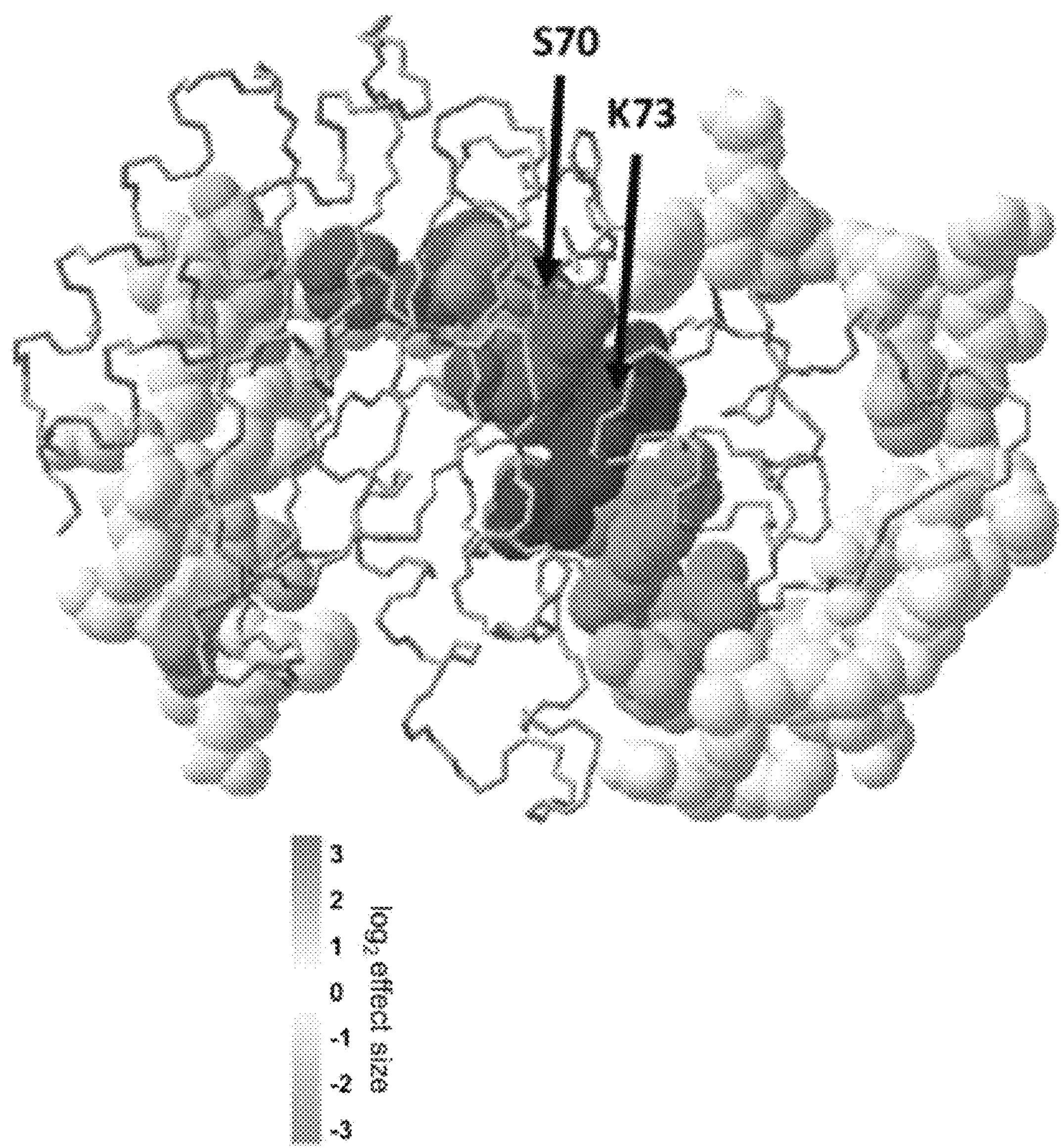
Figure 5:
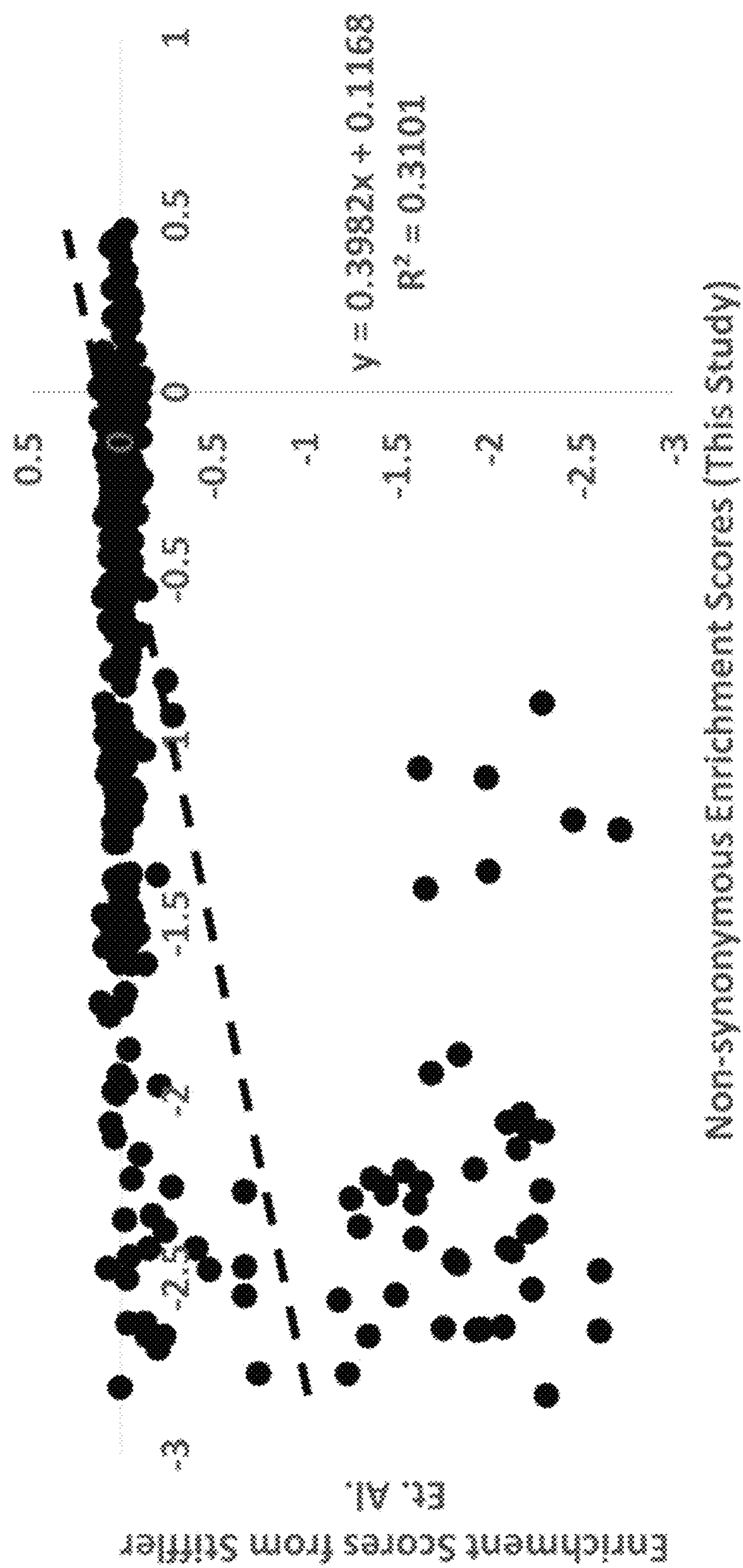
FIG. 5 depicts the correlation between effect-sizes for ampicillin mutations observed in this study and those reported previously. As observed in the previous study of TEM-1 β-lactamase, mutations generally fell into a bimodal distribution of either "damaging" or "not damaging".

Using this SAS mutagenized library, we then assessed the functional impact of this set of mutations present within the first 217 bp of the AmpR gene. The SAS library was then submitted to selection by both 50 μg/ml kanamycin and 200 μg/ml ampicillin. This dual selection allowed all bacteria to contain a plasmid without hindering selection based on ampicillin. Sequencing revealed a strong depletion of mutations resulting in non-synonymous compared to synonymous amino acid substitutions in the ampicillin-selected pool ($p<3\times10^{-15}$, Mann-Whitney U) with even stronger depletion of mutations resulting in non-conservative amino acid changes (i.e. hydrophobic to polar, etc) compared to synonymous changes ($p<2\times10^{-20}$, Mann-Whitney U) and compared to conservative amino acid changes ($p<2\times10^{-4}$, Mann-Whitney U) (FIG. 2A). Specific residues within the β-lactamase active site (S70 and K73) were among the most strongly depleted (average log 10 effect size for non-synonymous variants at these two sites was >2) with effect sizes dropping off further away from the active site (FIG. 2B). We compared the measured functional effects of β-lactamase mutations generated using our SAS library to those described previously, and observed a strong correlation of enrichment scores ($r^2$=0.31) largely owing to a consistent bifurcation of β-lactamase variants into those that reduce resistance and those with little effect (FIG. 5).

Figure 6:
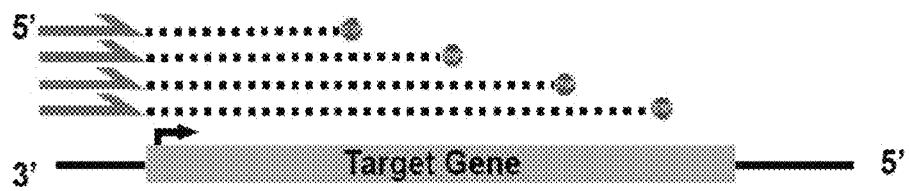
FIG. 6 depicts an extended schematic and library characteristics of SAS mutagenesis. Schematic of SAS mutagenesis: 1) Linear amplification of a target genomic region is performed using a mixture of dNTPs and reversibly-terminated dITP and a biotinylated primer. 2) The termination of products from step 1 is reversed and products are extended using the original template. 3) Reverse primer is added for one cycle, products are hybridized with streptavidin coated magnetic beads and washed to remove template. PCR is then performed to introduce single point mutations complementary to each inosine on the forward strand and to add a 20-mer unique molecular identifier (UMI) for the purpose of validating library creation. 4) Products are then cloned to reduce library complexity. 5) Minimal cycles of PCR are then used to amplify overlapping sections, each containing the UMI to perform subassembly of the SAS library.
Figure 6:
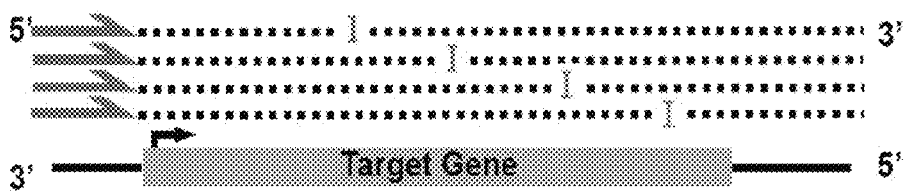
Figure 6:
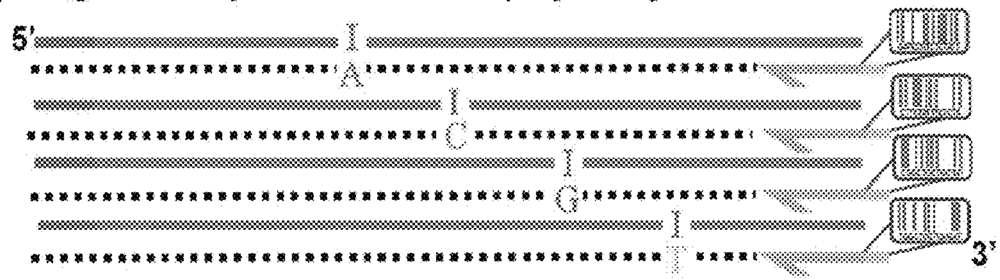
Figure 6:
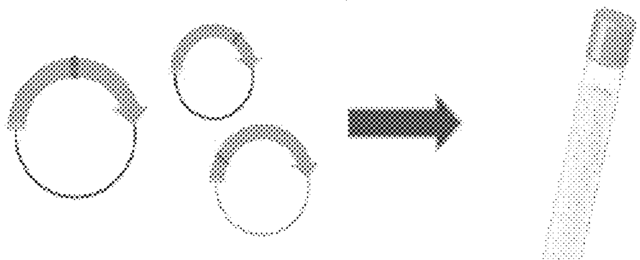
Figure 6:
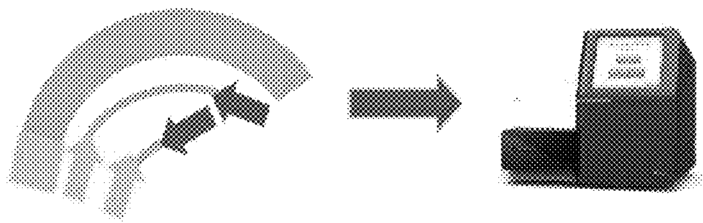
Figure 7:
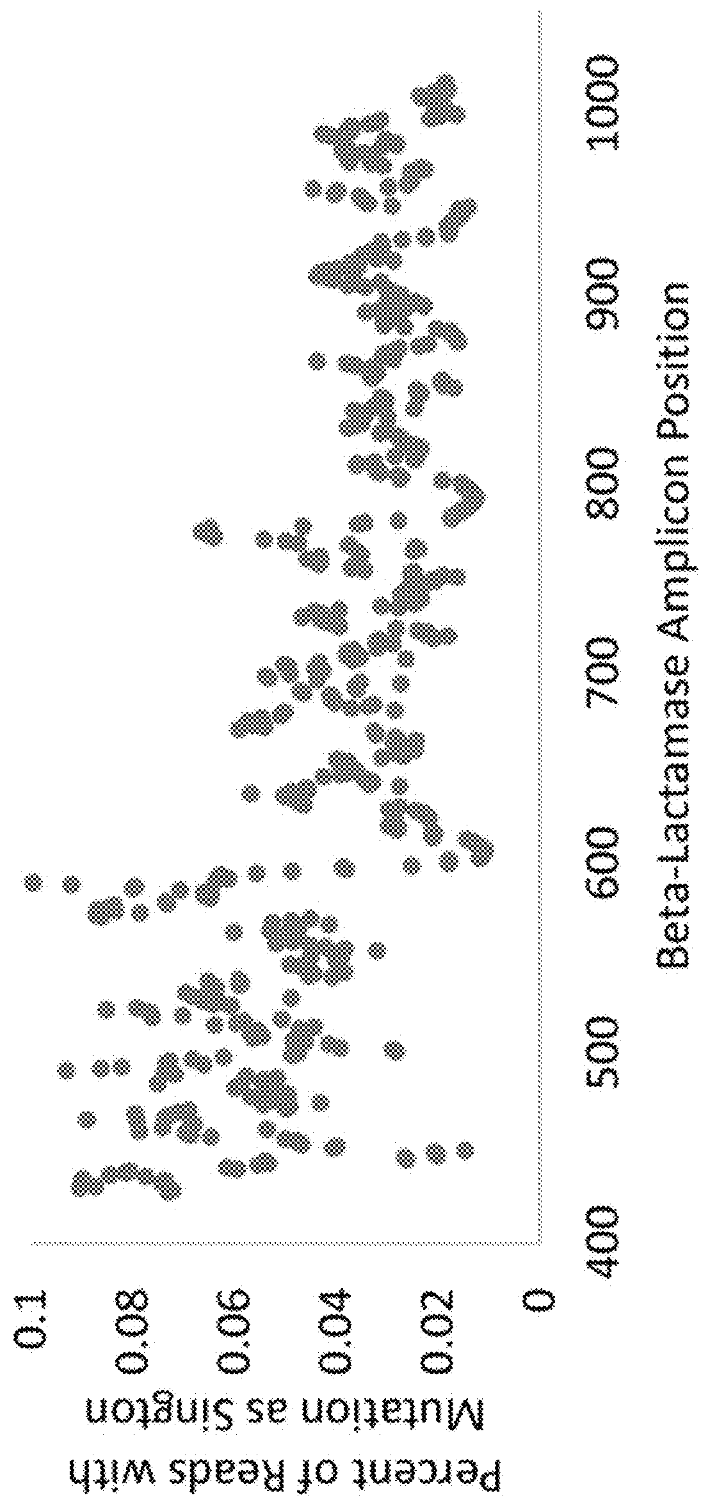
FIG. 7 depicts the distribution of mutations in a long SAS mutation library. Plotted is the total number of reads harboring a mutation as a singleton (i.e. a molecule with only one mutation) at each position along the long SAS mutation library created using the TEM-1 β-lactamase gene. PCR of the distal three sections totaling 607 bp was performed. Paired-end reads, one harboring the UMI barcode and the other harboring a segment of the SAS library, was sequenced on an Illumina MiSeq lane.

To validate the consistency of the SAS mutagenesis reaction across long segments of DNA, we next sequenced the distal 687 bp segment of the AmpR gene. In order to sequence the whole 687 bp segment, we appended unique molecular identifiable (UMI) sequences via primers with 20-mer random sequences followed by a universal 5' overhang during the final PCR amplification. To sequence the SAS library, we created overlapping PCR products of 687 bp, 511 bp and 330 bp using a universal 3' primer and 3 different 5' primers at varying distances from the 3' primer (FIG. 6). Sequencing reads obtained from these PCR products were then collapsed based on their UMI and variants were called using the consensus sequence for all barcodes with >20 reads for each section. Analysis of mutations observed within each region of this long SAS library showed similar rates of singleton mutations (32.5% or ~5% singleton mutant molecules per 100 bp mutated). This was comparable to the rate observed for the 3' end of the SAS library and consistent with an inosine incorporation rate of approximately 0.1 per by with slight drop-off along the length of the SAS library out to approximately 1 kb (FIG. 7). The rate of incorporation of each nucleotide was also comparable to that observed for the first 200 bp of the SAS library. These data suggest that long SAS libraries can be created without substantial change in mutagenic properties along the length of the product.

Mutagenesis using rtITP enables the construction of comprehensive libraries containing all possible single nucleotide changes within a region of DNA in less than a day for a fraction of the cost of current methods without the need to generate oligonucleotide libraries. The advantages of the SAS method include that there is no need for a complicated design process or the large expense of microarrays. While saturation mutagenesis of splice-sites and coding genes can now be performed at their native loci using CRISPR-Cas9 technologies, these experiments have thus far been limited due to size restrictions of oligonucleotide arrays. SAS mutagenesis will enable rapid, cost-effective production of homology-directed repair template pools to assess the functional impact of many single nucleotide changes within coding and non-coding loci simultaneously in a single experiment with fewer size restrictions. Although we have shown that SAS libraries of approximately 1 kb can be created, the reliance of this method on cycle termination may result in size limitations similar to Sanger sequencing. Longer mutational libraries may be created by modifications of the method, including titration of rtITP concentration or pooling of several reactions with varying concentrations of rtITP. Overall, the integration of SAS mutagenesis with high-throughput functional testing will enable the rapid assessment and fine-scale understanding of the millions of DNA variants present within the human population.

Methods for Example 1

Production of Reversibly-Terminated Deoxyinosine Triphosphate

Figure 4:
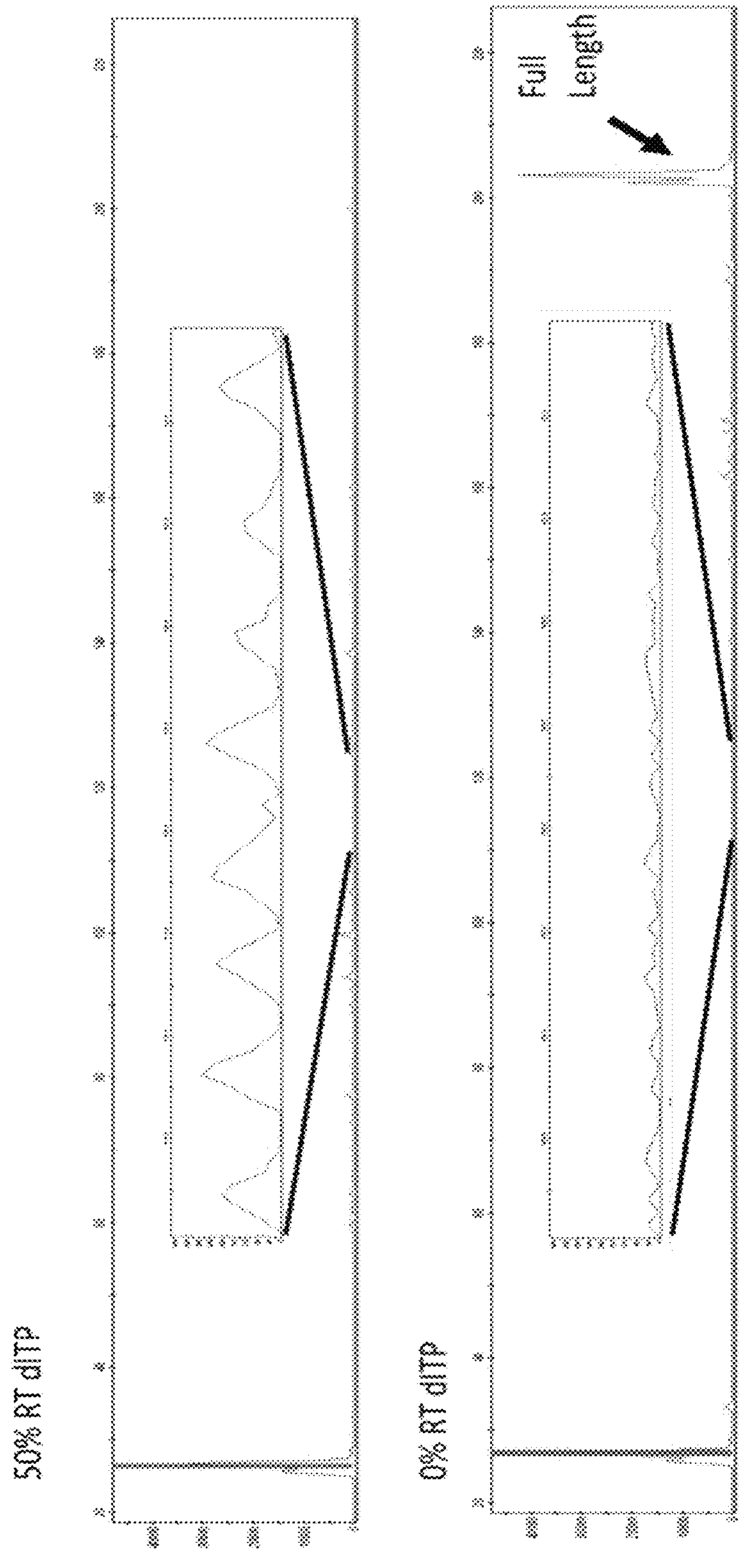
FIG. 4 depicts a demonstration of incorporation of reversibly-terminated deoxyinosine triphosphate (rtITP). Linear amplification of a 212 bp PCR product template with a fluorescently-labeled primer (ROX) was performed. Products were cleaned using ethanol precipitation and run on a 3730 Applied Biosystems capillary sequencer. Peak on left hand side is primer. Peak on right hand side is full length product. Peaks at every possible nucleotide as estimated with size markers were detected.

3'-O—NH2-deoxyadenosine triphosphate (Firebird Biomolecular Sciences, LLC) was enzymatically converted to 3'-O—NH2-deoxyinosine triphosphate by the sequential addition and heat inactivation of recombinant shrimp alkaline phosphatase (rSAP) (New England Biolabs) to create 3'-O—NH2-deoxyadenosine, deamination with adenosine deaminase (Sigma) to create 3'-O—NH2-deoxyinosine and a mixture of T4 PNK, pyruvate kinase and myokinase (adenylate kinase) to create 3'-O—NH2-deoxyinosine triphosphate. This product is then used directly in the SAS mutagenesis protocol. The ability of rtITP molecules to be incorporated into linear amplification products and terminate polymerase extension was tested using a 5'-ROX-labeled primer identical in sequence to the biotinylated primer used to perform SAS mutagenesis on the AmpR gene. Fluorescently labeled linear amplification products were produced using either dNTPs only that resulted in full length product or a 1:1 ratio of dNTPs to rtITP that resulted in partial length products terminating at each nucleotide (FIG. 4).

SAS Mutagenesis:

Linear amplification of target DNA was performed using a biotinylated primer, a 1:1 ratio of dNTPs and rtITP and Firebird Taq 475 (Firebird Biomolecular Sciences, LLC). This polymerase was specifically developed to incorporate 3'-O—NH2 linked nucleotides. The products were then bound to streptavidin beads and washed. Beads were then exposed to 70 mM Sodium Nitrite, pH 5.5 to reverse the termination, washed and cycle extended in the presence of template DNA. Upon extension, beads were washed and DNA eluted using 0.1 M NaOH followed by neutralization with 1 M Tris-HCl. Beads with bound DNA were then used as the DNA template for a PCR to produce final mutagenized products with randomly inserted nucleotides (A, C, G, and T) in place of each inosine. A detailed protocol can be found in Example 2.

Cloning and functional selection of TEM-1 β-lactamase: A dual selection plasmid (plasmid pGH1) was created by cloning the full TEM-1 β-lactamase gene amplified from plasmid pCMV6-XL6 into the plasmid pCR-Blunt-II-TOPO which contains the kanamycin resistance gene. A 217 bp segment containing the active site was then amplified from plasmid pGH1 containing both the AmpR and the KanR genes and SAS mutagenesis was performed on it as described above. The inverse of 217 bp segment within plasmid pGH1 was then amplified using primers that were the reverse complement of those used to amplify the 217 bp fragment. This PCR product was then Gibson assembled with the SAS library derived from the 217 bp fragment. This plasmid library was then transformed into XL10-Gold ultracompetent cells and grown in LB to saturation in the presence of 50 μg/ml kanamycin. For ampicillin selection, kanamycin outgrowth was diluted 1:1000 in 100 ml of selective media containing 200 μg/ml ampicillin. Cells were cultured for 2 hours, centrifuged, washed by resuspending in 1 ml LB without antibiotic, centrifuged and washed again, then resuspended in 5 ml LB media without antibiotic and grown overnight to saturation. Plasmids were purified using Qiagen Mini Plasmid purification kit.

Sequencing and Enrichment Analysis:

Mutated segments were sequenced in both directions with 250 bp paired-end reads using an Illumina MiSeq. The consensus sequence of each read-pair was aligned using Novoalign. Mutation counts were obtained from pileups of aligned consensus sequencing reads. Enrichment scores were determined using the following formula for each observed mutation.

$$F_i^a = \log_{10}\left[\frac{N_i^{a,sel}}{N_i^{a,unsel}}\right] - \log_{10}\left[\frac{N_i^{wt,sel}}{N_i^{wt,unsel}}\right]$$

For validation, enrichment scores were compared to those observed previously for mutations in the TEM-1 β-lactamase gene using linear regression of enrichments scores compared to scores obtained previously. Projection of enrichment scores onto the crystal structure of TEM-1 β-lactamase (PBD:1 FQG) was performed using Swiss-PBD viewer 4.1.0.

REFERENCES FOR EXAMPLE 1

1. Haller G, Li P, Esch C, Hsu S, Goate A M, Steinbach J H. Functional characterization improves associations between rare non-synonymous variants in CHRNB4 and smoking behavior. PloS one. 2014; 9(5):e96753.
2. Findlay G M, Boyle E A, Hause R J, Klein J C, Shendure J. Saturation editing of genomic regions by multiplex homology-directed repair. Nature. 2014; 513(7516):120-3.
3. Kitzman J O, Starita L M, Lo R S, Fields S, Shendure J. Massively parallel single-amino-acid mutagenesis. Nature methods. 2015; 12(3):203-6, 4 p following 6.
4. Patwardhan R P, Hiatt J B, Witten D M, Kim M J, Smith R P, May D, et al. Massively parallel functional dissection of mammalian enhancers in vivo. Nature biotechnology. 2012; 30(3):265-70.
5. Patwardhan R P, Lee C, Litvin O, Young D L, Pe'er D, Shendure J. High-resolution analysis of DNA regulatory elements by synthetic saturation mutagenesis. Nature biotechnology. 2009; 27(12):1173-5.
6. Starita L M, Young D L, Islam M, Kitzman J O, Gullingsrud J, Hause R J, et al. Massively Parallel Functional Analysis of BRCA1 RING Domain Variants. Genetics. 2015; 200(2):413-22.
7. Smith R P, Taher L, Patwardhan R P, Kim M J, Inoue F, Shendure J, et al. Massively parallel decoding of mammalian regulatory sequences supports a flexible organizational model. Nature genetics. 2013; 45(9)1021-8.
8. Cirino P C, Mayer K M, Umeno D. Generating mutant libraries using error-prone PCR. Methods in molecular biology. 2003; 231:3-9.
9. Copp J N, Hanson-Manful P, Ackerley D F, Patrick W M. Error-prone PCR and effective generation of gene variant libraries for directed evolution. Methods in molecular biology. 2014; 1179:3-22.
10. McCullum E O, Williams B A, Zhang J, Chaput J C. Random mutagenesis by error-prone PCR. Methods in molecular biology. 2010; 634:103-9.
11. Gao Y, Zhao H, Lv M, Sun G, Yang X, Wang H. [A simple error-prone PCR method through dATP reduction]. Wei sheng wu xue bao=Acta microbiologica *Sinica*. 2014; 54(1):97-103.
12. Stiffler M A, Hekstra D R, Ranganathan R. Evolvability as a function of purifying selection in TEM-1 beta-lactamase. Cell. 2015; 160(5):882-92.

Example 2

Protocol for SAS Mutagenesis Using Reversibly-Terminated Inosine

Creation of 3'-O—NH2, 2'-deoxyinsoine triphosphate:

Starting with 1 μl of 100 mM 3'-O—NH2, 2'-deoxyadenosine triphosphate (rtATP) (of which we purchased 5 μmoles total, i.e. 50 μl from Firebird Biomolecular Sciences, LLC), rSAP treat the rtATP for 1 hr at 37 deg. The reaction is 1 μl rtATP, 1 μl cutsmart buffer and 8 μl water (for a total of 10 μl). Inactivate the rSAP by denaturing at 95 deg for 20 min. This product can then be used as the substrate for the next kinase reaction. Add 2 μl of 10×T4 ligase buffer and 2 μl of T4 PNK buffer, 1 μl T4 PNK, 5 μl of pyruvate kinase (diluted in water and stored at −20 deg) and 5 μl of myokinase (adenylate kinase) (diluted in water and stored at −20). Both enzymes are ~5 U/μl. The total reaction is now 25 μl and the concentration of the rtITP should be 4 mM. This can be added directly to PCR reactions with no adverse effects.

Linear Amplification of Targets with rtITP:

Using a biotinylated primer, perform a PCR with 50% rtITP.

16 μl $H_2O$
5 μl 5×GoTaq Flexi Buffer (colorless)
1 μl 4 mM dNTPs (~1 μg/μl)
1 μl 4 mM rtITP (~1 μg/μl)
1 μl 10 μM biotinylated F primer
0.4 μl Firebird Taq 475
1 μl (200 ng/μl) Template
25 μl TOTAL Perform default PCR conditions on ABI thermocycler (25 cycles). Note: This will produce 25× more product than template (assuming the primers and dNTPs are in excess), which means that the product is 1×dsDNA and 25×ssDNA that has been randomly terminated. It is important to store beads in 1×TE for the stability of the ssDNA.

Bind Biotinylated DNA to DYNA Beads (Streptavidin Coated):

Take 10 μl of streptavidin coated beads and remove supernatant using a magnet in a Lo-Bind tube. Wash beads in 200 μl Binding buffer (see Reagents at end of protocol) in a Lo-Bind tube. Add 150 μl Binding Buffer linear amplification product and transfer to washed beads. Incubate 30 min at room temp, rocking. Wash 1× with 200 μl Wash buffer 1, 15 min room temp rocking. Pre-warm Wash Buffer 2 to 65 C. Perform next 3 washes one at a time to keep solutions at 65 C. Wash 3× with 200 μl Wash buffer 2, resuspend by pipetting, and incubate 15 min at 65 C. Resuspend in 1×TE. Beads are stable at this step if you choose to pause here.

Reverse Termination of rtITP and Extension:

Note: 5 min of exposure of rtATP to 700 mM sodium nitrite, pH 5.5 will enable PCR amplification in the absence of dATP, thus proving that it reverses the termination sufficiently enough to allow use in PCR. Take beads resuspended in 1×TE and remove TE. Add 20 μl of 700 mM sodium nitrite, pH 5.5. Allow to sit for 5 min (not longer). Prolonged exposure may damage DNA. Remove sodium nitrite, wash 3× with TE and add PCR reaction containing:

All Streptavidin beads
18 μl $H_2O$
20 μl 2×NEB Next HF Mastermix
1 μl 10 mM dNTPs
1 μl (200 ng/μl) Template
40 μl TOTAL Perform default PCR conditions on ABI thermocycler (8 cycles). Note: Each additional cycle allows a different set of unextended products to find a template and extend. If one chooses to perform only 1 cycle or fewer cycles, we suggest adding sufficient template such that all of the unexpended products have a template. Theoretically, after a few cycles all of the unextended product will have had a chance to sit down on a full length template and extend.

Removal of Template DNA:

In order to make sure one is not just amplifying the template, plasmids can be degraded with DPN1 enzyme if obtained directly from bacteria and DNA amplified with deoxyuricil can be degraded with uracil-DNA-glycosylase and exonuclease VIII. If these are not true of the template, having used a biotinylated primer is the only way to get rid of the template. To do this, add 1 μl of the R primer only and amplify for 2 additional cycles.

Then: Wash 1× with 200 μl Wash buffer 1, 15 min room temp rocking. Pre-warm Wash Buffer 2 to 65 C. Perform next 3 washes one at a time to keep solutions at 65 C. Wash 3× with 200 μl Wash buffer 2, resuspend by pipetting, and incubate 15 min at 65 C. Resuspend in 1×TE. Beads are stable at this step if you choose to pause here.

Amplify from Beads:

All Streptavidin beads

17 μl $H_2O$

20 μl 2×NEB Next HF Mastermix

1 μl 10 mM dNTPs

1 μl F primer (not biotinylated)

1 μl R primer

40 μl TOTAL

Perform default PCR conditions on ABI thermocycler (25 cycles). Purify either using a Qiagen PCR cleanup kit or AmPure beads with ½ 50% 3350 glycerol and ½ 5 M NaCl.

Reagents:

Streptavidin Bead Binding Buffer: 10 mM Tris-HCL (pH 7.5), 1 mM EDTA (pH 8) and 1 M NaCl Wash Buffer 1: 1×SSC with 0.1% SDS Wash Buffer 2: 0.1×SSC with 0.1% SDS Elution Buffer: 0.1 M NaOH (use only if you want to ensure there is no template)

Reference:

Labeled nucleoside tri phosphates with reversibly terminating aminoalkoxyl groups. Nucleosides, Nucleotides and Nucleic Acids 2010; 29: 879-895.

What is claimed is:

1. A method of generating a mutational library of a target nucleic acid, the method comprising:

a) creating a reaction mixture comprising the target nucleic acid, polymerase, a forward primer, deoxynucleotide triphosphates (dNTPs) and universal base triphosphates comprising a blocking group;

b) performing linear PCR, wherein the linear PCR generates products of various lengths, wherein each product comprises about 1 universal base comprising a blocking group, and wherein the linear PCR stops after incorporating the universal base triphosphate comprising a blocking group;

c) removing the blocking group from the universal base incorporated into the linear product;

d) extending the products from (c) with polymerase, wherein the extension products comprise about 1 universal base incorporated therein; and e) performing exponential PCR, wherein the products from (d) are amplified and wherein the products comprise a single point mutation in the location where the universal base was incorporated; and wherein the products of the exponential PCR make up a mutational library of the target nucleic acid comprising a plurality of products each comprising a single point mutation, wherein the point mutations are evenly distributed throughout the products of the mutational library.

2. The method of claim 1, wherein the universal base is selected from the group consisting of 3-nitropyrrole, 5-nitroindole, and 2'-dexoyinosine.

3. The method of claim 1, wherein the universal base is 2'-dexoyinosine.

4. The method of claim 1, wherein the blocking group is 3'-O—$NH_2$.

5. The method of claim 1, wherein the forward primer is biotinylated.

6. The method of claim 1, wherein the deoxynucleotide triphosphates (dNTPs) and universal base triphosphates are added to the reaction mixture in a 1:1 ratio.

7. The method of claim 1, wherein the product in step (b) comprises 1 universal base comprising a blocking group.

8. The method of claim 1, wherein the linear PCR product produced in step (b) is isolated prior to removing the blocking group in step (c).

9. The method of claim 1, wherein the forward primer is biotinylated and the linear product produced in step (b) is isolated via streptavidin beads prior to removing the blocking group in step (c).

10. The method of claim 4, wherein the blocking group is removed by exposure to 70 mM sodium nitrite buffer, pH 5.5.

11. The method of claim 1, wherein the target nucleic acid is degraded prior to step (e).

12. The method of claim 1, wherein more than 30% of the products of the exponential PCR comprise a single point mutation relative to the target nucleic acid.

13. The method of claim 1, wherein less than 2% of the products of the exponential PCR comprise more than a single point mutation relative to the target nucleic acid.

14. A method of making 2'-deoxy, 3'-O—$NH_2$ inosine triphosphate from 2'-deoxy, 3'-O—$NH_2$ adenosine triphosphate, the method comprising:

a) dephosphorylating 2'-deoxy, 3'-O—$NH_2$ adenosine triphosphate with a phosphatase;

b) deaminating the product from (a) with a deaminase; and c) phosphorylating the product from (b) with three different kinases.

15. The method of claim 14, wherein the phosphatase is shrimp alkaline phosphatase.

16. The method of claim 14, wherein step (a) occurs for about 1 hour at about 37° C.

17. The method of claim 14, wherein after step (a) and prior to step (b) the phosphatase is denatured.

18. The method of claim 14, wherein the deaminase is adenosine deaminase.

19. The method of claim 14, wherein step (b) is performed in 50 mM postassium phosphate buffer.

20. The method of claim 14, wherein the three different kinases are adenylate kinase, T4 polynucleotide kinase and pyruvate kinase.

* * * * *